United States Patent [19]

Fischer

[11] 3,933,467

[45] Jan. 20, 1976

[54] SUBSTITUTED NITROANILINES AND SUBSTITUTED 1, 3, 5-TRIAZINES AS HERBICIDAL MIXTURES

[75] Inventor: Adolf Fischer, Mutterstadt, Germany

[73] Assignee: BASF Aktiengesellschaft, Ludwigshafen (Rhine), Germany

[22] Filed: May 23, 1974

[21] Appl. No.: 472,646

Related U.S. Application Data

[63] Continuation-in-part of Ser. No. 162,317, July 13, 1971, Pat. No. 3,849,107.

[30] Foreign Application Priority Data

July 28, 1970 Germany............................ 2037265

[52] U.S. Cl........................................ 71/93; 71/121
[51] Int. Cl.².......................................... A01N 9/22
[58] Field of Search................................. 71/93, 121

[56] References Cited

UNITED STATES PATENTS

| 3,518,076 | 6/1970 | Wright | 71/121 |
| 3,617,251 | 11/1971 | Hunter | 71/121 |
| 3,617,252 | 11/1971 | Hunter | 71/121 |
| 3,676,441 | 7/1972 | Nikles | 71/93 |
| 3,752,661 | 8/1973 | Orlett | 71/103 |

Primary Examiner—Lewis Gotts
Assistant Examiner—Catherine L. Mills
Attorney, Agent, or Firm—Johnston, Keil, Thompson & Shurtleff

[57] ABSTRACT

Controlling unwanted plant growth with mixtures of substituted nitroanilines and substituted 1, 3, 5-triazines in a preferred weight ratio of 3:1 to 1:3.

2 Claims, No Drawings

SUBSTITUTED NITROANILINES AND SUBSTITUTED 1, 3, 5-TRIAZINES AS HERBICIDAL MIXTURES

RELATED APPLICATION

This application is a continuation-in-part of my co-pending application Ser. No. 162,317, filed July 13, 1971, now U.S. Pat. No. 3,849,107, issued November 19, 1974. The present invention relates to herbicides, particularly selective herbicides, which are suitable for controlling the growth of unwanted plants in crop plants.

If is known to use substituted dinitroaniline derivatives, phosphoric acids, pyridazones, substituted ureas, triazines and biscarbamates as herbicidal active ingredients. However, their action is not always satisfactory.

I have now found that herbicides comprising a mixture of a. a compound of the formula

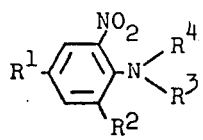

where $R^1$ denotes hydrogen, nitro, alkyl, trifluoromethyl or methylsulfonyl, $R^2$ denotes nitro, alkyl, trifluoromethyl or methylsulfonyl, $R^3$ and $R^4$ are identical or different and denote hydrogen, a linear or branched, saturated or unsaturated aliphatic radical which may be substituted by halogen, cyano, alkoxy or azido, or haloacetyloxyalkyl or alkylcarbamoyloxyalkyl, and $R^3$ and $R^4$, together with the nitrogen atom whose substituents they are, may also form a hexamethylenimine ring, with b. a compound of the formula

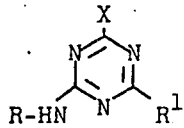

where R denotes alkyl or cyanoalkyl, $R^1$ denotes alkylamino, thioalkyl, butynylamino or azido, and X denotes halogen, alkoxy, thioalkyl or azido, have a good herbicidal action, both pre- and postemergence, on weeds such as Chenopodium album, Galinsoga parviflora, Sinapis arvensis, Polygonum spp., Amaranthus spp., and Portulaca oleracea; on grassy weeds such as Poa spp., Bromus spp., Avena sativa and Cyperus spp.; and on millet types such as Panicum spp., Setaria spp., Digitaria spp., and Echinochloa spp. in the following crops: Gossypium spp., Soja hispida, Brassica napus, Beta spp., and Oryza sativa.

The individual active ingredients may be mixed together in any desired ratio; however, mixtures in which the ratio by weight of a to b is from 3:1 to 1:3 are preferred.

The agents according to the invention may be used as solvents, emulsions, suspensions or dusts. The form of application depends entirely on the purpose for which the agents are being used; in any case it should ensure a fine distribution of the active ingredient.

For the preparation of solutions to be sprayed direct, hydrocarbons having boiling points higher than 150°C, e.g. tetrahydronaphthalene or alkylated naphthalenes, or organic liquids having boiling points higher than 150°C and having one or more than one functional group, e.g. the keto group, the ether group, the ester group or the amide group, this group or these groups being attached as substituent(s) to a hydrocarbon chain or being a component of a heterocyclic ring, may be used as spray liquids.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g. polyethylene oxide adducts. Concentrates which are suitable for dilution with water may be prepared from active ingredient, emulsifying or dispersing agent and possibly solvent.

Dusts may be prepared by mixing or grinding the active ingredients with a solid carrier, e.g. kieselguhr, talc, clay or fertilizers.

To improve the action, wetting agents and adhering agents or oils may also be added.

EXAMPLE 1

In a greenhouse, loamy sandy soil was filled into pots and sown with Gossypium hirsutum, Digitaria sanguinalis, Echinochloa crus-galli, Amaranthus retroflexus and Portulaca oleracea. The soil prepared in this manner was subsequently treated with the following amounts of the following individual active ingredients and mixtures of them, each active ingredient and each mixture being dispersed of emulsified in 500 liters of water per hectare:

I N-allyl-N-β-chloroethyl-2,6-dinitro-4-trifluoromethylaniline, 2 and 4 kg per hectare;

II N-propyl-N-β-chloroethyl-2,6-dinitro-4-trifluoromethylaniline, 1 and 3 kg per hectare;

III N', N-dipropyl-2,6-dinitro-4-trifluoromethylaniline, 1.5 and 3 kg per hectare;

IV 2-chloro-4-ethylamino-6-butyn-1-yl-3-amino-1,3,5-triazine, 2 and 3 kg per hectare;

V 2-chloro-4-ethylamino-6-methoxyisopropylamino-1,3,5-triazine, 1.5 and 3 kg per hectare;

VI 2-thiomethyl-4,6-diisopropylamino-1,3,5-triazine, 2 and 4 kg per hectare;

I + VI : 2 + 2 kg per hectare;

II + IV : 1 + .2 kg per hectare;

III + V : 1.5 + 1.5 kg per hectare.

After 4 to 5 weeks it was ascertained that the mixtures had a stronger herbicidal action than the individual active ingredients, combined with more favorable crop plant compatibility.

The results of the experiment are given in the following table.

Table

|  | I | I | III | IV | V | VI | I+VI | II+IV | III+V |
|---|---|---|---|---|---|---|---|---|---|
| kg/ha | 2 4 | 1 3 | 1.5 3 | 2 3 | 1.5 3 | 2 4 | 2 + 2 | 1 + 2 | 1.5 + 1.5 |

Table -continued

|  | I |  | III |  | IV |  | V |  | VI |  | I+VI | II+IV | III+V |
|---|---|---|---|---|---|---|---|---|---|---|---|---|---|
| Gossypium hirsutum | 0 | 15 | 0 | 20 | 0 | 20 | 5 | 15 | 5 | 25 | 0 | 20 | 0 | 0 | 0 |
| Digitaria sanguinalis | 80 | 100 | 85 | 100 | 80 | 100 | 65 | 85 | 75 | 80 | 45 | 85 | 100 | 100 | 100 |
| Echinochloa crus-galli | 85 | 100 | 85 | 100 | 85 | 100 | 60 | 90 | 45 | 80 | 50 | 90 | 100 | 100 | 100 |
| Amaranthus retroflexus | 25 | 80 | 25 | 70 | 20 | 60 | 65 | 90 | 70 | 100 | 70 | 100 | 100 | 100 | 100 |
| Portulaca oleracea | 30 | 80 | 25 | 70 | 25 | 55 | 60 | 100 | 70 | 100 | 60 | 100 | 100 | 100 | 100 |

0 = no damage
100 = complete destruction

The action of the following mixtures corresponds to that of those above:

N,N-dipropyl-2,6-dinitro-4-methylsulfonylaniline;
N-ethyl-N-butyl-2,6-dinitro-4-methylsulfonylaniline;
N-β-methoxyethyl-N-β-chloroethyl-2,6-dinitro-4-trifluoromethylaniline;
N-β-methoxyethyl-N-β-azidoethyl-2,6-dinitro-4-trifluoromethylaniline;
N-propyl-N-β-cyanoethyl-2,6-dinitro-4-trifluoromethylaniline;
N-ethyl-N-β-chloroethyl-2,6-dinitro-4-trifluoromethylaniline;
N-ethyl-N-butyl-2,6-dinitro-4-trifluoromethylaniline;
N-isobutyl-N-β-cyanoethyl-2,6-dinitro-4-trifluoromethylaniline;
N-ethyl-N-β-cyanoethyl-2,6-dinitro-4-trifluoromethylaniline;
N-methyl-N-β-cyanoethyl-2,6-dinitro-4-trifluoromethylaniline;
N-β-methoxyethyl-N-β-cyanoethyl-2,6-dinitro-4-trifluoromethylaniline;
N-butyl-N-β-cyanoethyl-2,6-dinitro-4-trifluoromethylaniline;
N-methyl-N-β-cyanoethyl-2,6-dinitro-4-trifluoromethylaniline;
N-butyl-N-β-chloropropyl-2,6-dinitro-4-trifluoromethylaniline;
N-butyl-N-γ-chloropropyl-2,6-dinitro-4-trifluoromethylaniline;
N-propyl-N-β-chloropropyl-2,6-dinitro-4-trifluoromethylaniline;
N-propyl-N-β-bromoethyl-2,6-dinitro-4-trifluoromethylaniline;
N,N-bis-β-(chloroethyl)-2,6-dinitro-4-trifluoromethylaniline;
N,N-bis-β-(chloroethyl)-2,6-dinitro-4-methylaniline;
N-propyl-N-allyl-4,6-dinitro-2-trifluoromethylaniline;
N-ethyl-N-β-azidoethyl-2,6-dinitro-4-trifluoromethylaniline;
N-propyl-N-β-azidoethyl-2,6-dinitro-4-trifluoromethylaniline;
N-propyl-N-β-(chloroacetyloxy)-ethyl-2,6-dinitro-4-trifluoromethylaniline;
N,N-bis-(β-chloroacetyloxy)-ethyl-2,6-dinitro-4-trifluoromethylaniline;
N-(β-chloroacetyloxy)-ethyl-2,6-dinitro-4-trifluoromethylaniline;
N-(β-methylcarbamoyloxy)-ethyl-2,6-dinitro-4-trifluoromethylaniline;
N-ethyl-N-β-bromoethyl-2,6-dinitro-4-trifluoromethylaniline;
N-β-methoxyethyl-N-β-bromoethyl-2,6-dinitro-4-trifluoromethylaniline;
N-γ-chloropropyl-N-β-chloroethyl-2,6-dinitro-4-trifluoromethylaniline;
N-propen-(1)-yl-(3)-N-β-chloroethyl-2,6-dinitro-4-methylaniline;
N-propyl-N-β-chloroethyl-2,6-dinitro-4-methylaniline;
N-propyl-N-β-azidoethyl-2,6-dinitro-4-methylaniline;
N-propyl-N-β-azidoethyl-2,6-dinitro-4-methylsulfonylaniline;
N-propyl-N-β-bromoethyl-2,6-dinitro-4-methylsulfonylaniline;
N-propyl-N-β-(chloroacetyloxy)-ethyl-2,6-dinitro-4-methylaniline;
N-propyl-N-β-(chloroacetyloxy)-propyl-2,6-dinitro-4-trifluoromethylaniline; or
N-propyl-N-β-(methylcarbamoyloxy)-propyl-2,6-dinitro-4-trifluoromethylaniline with 2-chloro-4-ethylamino-6-butyn-1-yl-3-amino-1,3,5-triazine;
2-chloro-4-ethylamino-6-methoxyisopropylamino-1,3,5-triazine;
2-chloro-4-ethylamino-6-α,α-dimethylpropargylamino-1,3,5-triazine;
2-chloro-4-isopropylamino-6-α,α-dimethylpropargylamino-1,3,5-triazine;
2-thiomethyl-4-ethylamino-6-butyn-1-yl-3-amino-1,3,5-triazine;
2-chloro-4-ethylamino-6-sec-butylamino-1,3,5-triazine;
2-chloro-4-ethylamino-6-α,α-dimethylcyanomethylamino-1,3,5-triazine;
2-chloro-4-isopropylamino-6-diethylamino-1,3,5-triazine;
2-methoxy-4-isopropylamino-6-ethylamino-1,3,5-triazine;
2-thiomethyl-4-isopropylamino-6-tert-butylamino-1,3,5-triazine; or
2-azido-4-sec-butylamino-6-thiomethyl-1,3,5-triazine.

EXAMPLE 2

An agricultural area was sown with Soja hispida, Digitaria sanguinalis, Bromus tectorum, Amaranthus retroflexus and Portulaca oleracea and subsequently treated with the following amounts of the following individual active ingredients and mixtures of them, each active ingredient and each mixture being dispersed or emulsified in 500 liters of water per hectare:

I   N-allyl-N-β-chloroethyl-2,6-dinitro-4-trifluoromethylaniline, 1 and 3 kg per hectare;
II   N-propyl-N-β-chloroethyl-2,6-dinitro-4-trifluoromethylaniline, 1 and 2 kg per hectare;
III   N,N-dipropyl-2,6-dinitro-4-trifluoromethylaniline, 1 and 3 kg per hectare;
IV   1-m-trifluoromethyl-4-dimethylamino-5-chloropyridazone-6, 2 and 3 kg per hectare;
V   1-phenyl-4,5-dimethoxypyridazone-6, 1 and 2 kg per hectare;
VI   1-m-methylphenyl-4-methoxy-5-bromopyridazone-6, 2 and 3 kg per hectare;

VII N-m-trifluoromethylphenyl-N-cyclohex-1-enyl-N',N'-dimethylurea, 2 and 3 kg per hectare;
VIII N,N-dimethyl-N'-[N''-methoxyisopropylcarbamoyloxyphenyl]-urea, 1 and 2 kg per hectare;
IX N-4-(p-chlorophenoxy)-phenyl-N',N-dimethylurea, 2 and 3 kg per hectare;
X 2-chloro-4-ethylamino-6-(α,α-dimethylcyanomethyl)-amino-1,3,5-triazine, 1 and 2 kg per hectare;
I + IV : 1 + 2 kg per hectare;
II + V : 1 + 1 kg per hectare;
III + VI : 1 + 2 kg per hectare;
I + VII : 1 + 2 kg per hectare;
II + VIII : 1 + 1 kg per hectare;
III + IX : 1 + 2 kg per hectare;
II + X : 1 + 1 kg per hectare.

After 4 to 5 weeks it was ascertained that the mixtures had a stronger herbicidal action than the individual active ingredients, combined with more favorable crop plant compatibility.

The results of the experiment are given in the following table:

N-propyl-N-β-chloropropyl-2,6-dinitro-4-trifluoromethylaniline;
N-propyl-N-β-bromoethyl-2,6-dinitro-4-trifluoromethylaniline;
N,N-bis-β-(chloroethyl)-2,6-dinitro-4-trifluoromethylaniline;
N,N-bis-β-(chloroethyl)-2,6-dinitro-4-methylaniline;
N-propyl-N-allyl-4,6-dinitro-2-trifluoromethylaniline;
N-ethyl-N-β-azidoethyl-2,6-dinitro-4-trifluoromethylaniline;
N-propyl-N-β-azidoethyl-2,6-dinitro-4-trifluoromethylaniline;
N-propyl-N-β-(chloroacetyloxy)-ethyl-2,6-dinitro-4-trifluoromethylaniline;
N,N-bis-(β-chloroacetyloxy)-ethyl-2,6-dinitro-4-trifluoromethylaniline;
N-(β-chloroacetyloxy)-ethyl-2,6-dinitro-4-trifluoromethylaniline;
N-(β-methylcarbamoyloxy)-ethyl-2,6-dinitro-4-trifluoromethylaniline;

Table

| | I | | II | | III | | | IV | | V | | VI | | VII | | VIII | | IX | | X | |
|---|---|---|---|---|---|---|---|---|---|---|---|---|---|---|---|---|---|---|---|---|---|
| kg/ha | 1 | 3 | 1 | 2 | 1 | 3 | 2 | 3 | 1 | 2 | 2 | 3 | 2 | 3 | 1 | 2 | 2 | 3 | 1 | 2 |
| Soja hispida | 0 | 15 | 0 | 10 | 0 | 20 | 0 | 15 | 0 | 20 | 0 | 10 | 0 | 20 | 0 | 20 | 5 | 25 | 0 | 20 |
| Digitaria sanguinalis | 70 | 100 | 85 | 100 | 70 | 100 | 65 | 95 | 55 | 90 | 50 | 75 | 80 | 100 | 45 | 85 | 60 | 90 | 30 | 75 |
| Bromus tectorum | 70 | 100 | 75 | 100 | 70 | 100 | 55 | 80 | 55 | 95 | 40 | 65 | 50 | 75 | 50 | 95 | 55 | 80 | 50 | 95 |
| Amaranthus retroflexus | 15 | 50 | 25 | 50 | 15 | 50 | 60 | 85 | 70 | 100 | 70 | 95 | 90 | 100 | 50 | 95 | 45 | 90 | 45 | 85 |
| Portulaca oleracea | 15 | 50 | 25 | 55 | 20 | 55 | 60 | 85 | 70 | 95 | 65 | 90 | 95 | 100 | 65 | 100 | 60 | 95 | 70 | 100 |

| kg/ha | I + IV 1 + 2 | II + V 1 + 1 | III + VI 1 + 2 | I + VII 1 + 2 | II + VIII 1 + 1 | III + IX 1 + 2 | II+X 1 +1 |
|---|---|---|---|---|---|---|---|
| Soja hispida | 0 | 0 | 0 | 0 | 0 | 0 | O |
| Digitaria sanguinalis | 100 | 100 | 100 | 100 | 100 | 100 | 100 |
| Bromus tectorum | 100 | 100 | 100 | 100 | 100 | 100 | 100 |
| Amaranthus retroflexus | 85 | 100 | 95 | 100 | 90 | 80 | 85 |
| Portulaca oleracea | 90 | 100 | 100 | 100 | 100 | 95 | 100 |

O = no damage
100 = complete destruction

The action of the following mixtures corresponds to that of those above:

N-β-methoxyethyl-N-β-chloroethyl-2,6-dinitro-4-trifluoromethylaniline;
N-β-methoxyethyl-N-β-azidoethyl-2,6-dinitro-4-trifluoromethylaniline;
N-propyl-N-β-cyanoethyl-2,6-dinitro-4-trifluoromethylaniline;
N-ethyl-N-β-chloroethyl-2,6-dinitro-4-trifluoromethylaniline;
N-ethyl-N-butyl-2,6-dinitro-4-trifluoromethylaniline;
N-isobutyl-N-β-cyanoethyl-2,6-dinitro-4-trifluoromethylaniline;
N-ethyl-N-β-cyanoethyl-2,6-dinitro-4-trifluoromethylaniline;
N-methyl-N-β-cyanoethyl-2,6-dinitro-4-trifluoromethylaniline;
N-β-methoxyethyl-N-β-cyanoethyl-2,6-dinitro-4-trifluoromethylaniline;
N-butyl-N-β-cyanoethyl-2,6-dinitro-4-trifluoromethylaniline;
N-methyl-N-β-cyanoethyl-2,6-dinitro-4-trifluoromethylaniline;
N-butyl-N-β-chloropropyl-2,6-dinitro-4-trifluoromethylaniline;
N-isobutyl-N-γ-chloropropyl-2,6-dinitro-4-trifluoromethylaniline;
N-ethyl-N-β-bromoethyl-2,6-dinitro-4-trifluoromethylaniline;
N-β-methoxyethyl-N-β-bromoethyl-2,6-dinitro-4-trifluoromethylaniline;
N-γ-chloropropyl-N-β-chloroethyl-2,6-dinitro-4-trifluoromethylaniline;
N-propen-(1)-yl-(3)-N-β-chloroethyl-2,6-dinitro-4-methylaniline;
N-propyl-N-β-chloroethyl-2,6-dinitro-4-methylaniline;
N-propyl-N-β-azidoethyl-2,6-dinitro-4-methylaniline;
N-propyl-N-β-azidoethyl-2,6-dinitro-4-methylsulfonylaniline;
N-propyl-N-β-bromoethyl-2,6-dinitro-4-methylsulfonylaniline;
N-propyl-N-β-(chloroacetyloxy)-ethyl-2,6-dinitro-4-methylaniline;
N-propyl-N-β-(chloroacetyloxy)-propyl-2,6-dinitro-4-trifluoromethylaniline; or
N-propyl-N-β-(methylcarbamoyloxy)-propyl-2,6-dinitro-4-trifluoromethylaniline with
2-thiomethyl-4-isopropylamino-6-tert-butylamino-1,3,5-triazine;
2-thiomethyl-4-isopropylamino-6-sec-butylamino-1,3,5-triazine;
2-thiomethyl-4-ethylamino-6-sec-butylamino-1,3,5-triazine;

2-chloro-4-ethylamino-6-sec-butylamino-1,3,5-triazine; or 2-chloro-4-methylamino-6-(α,α-dimethylcyanomethyl)-amino-1,3,5-triazine.

After 4 to 5 weeks it was observed that the mixtures had a better herbicidal action than the individual active ingredients and the same compatibility with the crop plants. The results of the experiment may be seen from the following Table.

Table

| Active ingredient | I | | | | II | | | | III | | | | IV | | | |
|---|---|---|---|---|---|---|---|---|---|---|---|---|---|---|---|---|
| kg/ha | 0.25 | 0.5 | 0.75 | 1.0 | 0.25 | 0.5 | 0.75 | 1.0 | 0.25 | 0.5 | 0.75 | 1.0 | 0.25 | 0.5 | 0.75 | 1.0 |
| Crop plants: | | | | | | | | | | | | | | | | |
| Gossypium hirsutum | 0 | 0 | 0 | 0 | 0 | 0 | 0 | 0 | 0 | 0 | 0 | 0 | 0 | 0 | 0 | 0 |
| unwanted plants | | | | | | | | | | | | | | | | |
| Digitaria sanguinalis | 25 | 45 | 60 | 85 | 5 | 16 | 20 | 30 | 10 | 18 | 25 | 35 | 10 | 20 | 30 | 40 |
| Echinochloa crus galli | 32 | 50 | 85 | 70 | 4 | 8 | 12 | 20 | 5 | 10 | 20 | 30 | 5 | 10 | 15 | 25 |
| Lamium amplexicaule | 0 | 0 | 0 | 5 | 25 | 45 | 60 | 80 | 20 | 35 | 50 | 75 | 28 | 50 | 65 | 80 |

0 = no damage
100 = complete destruction

Table

| Active ingredient | V | | | | I+II | | | I+III | | |
|---|---|---|---|---|---|---|---|---|---|---|
| kg/ha | 0.25 | 0.5 | 0.75 | 1.0 | 0.25+0.75 | 0.75+0.25 | 0.5+0.5 | 0.25+0.75 | 0.75+0.25 | 0.5+0.5 |
| Crop plants | | | | | | | | | | |
| Gossypium hirsutum | 0 | 0 | 0 | 0 | 0 | 0 | 0 | 0 | 0 | 0 |
| Unwanted plants | | | | | | | | | | |
| Digitaria sanguinalis | 14 | 20 | 25 | 32 | 90 | 98 | 98 | 90 | 100 | 98 |
| Echinochloa crus galli | 4 | 10 | 14 | 20 | 85 | 95 | 95 | 90 | 97 | 95 |
| Lamium amplexicaule | 15 | 30 | 35 | 40 | 90 | 80 | 90 | 85 | 75 | 80 |

0 = no damage
100 = complete destruction

Table

| Active ingredient kg/ha | I+IV | | | I+V | | |
|---|---|---|---|---|---|---|
| | 0.25+0.75 | 0.75+0.25 | 0.5+0.5 | 0.25+0.75 | 0.75+0.25 | 0.5+0.5 |
| Crop plants | | | | | | |
| Gossypium hirsutum | 0 | 0 | 0 | 0 | 0 | 0 |
| Unwanted plants | | | | | | |
| Digitaria sanguinalis | 95 | 100 | 100 | 100 | 100 | 100 |
| Echinochloa crus galli | 85 | 96 | 100 | 100 | 96 | 100 |
| Lamium amplexicaule | 97 | 78 | 96 | 75 | 65 | 70 |

0 = do damage
100 = total destruction

EXAMPLE 3

In a greenhouse experimental pots were filled with loamy sandy soil and sown with various seeds. The soil prepared in this way was then treated with the following individual active ingredients and mixtures thereof as an emulsion-dispersion:

I  N-propyl-N-β-chloroethyl-2,6-dinitro-4-trifluoromethylaniline
II  2-methylmercapto-4,6-diisopropylamino-1,3,5-triazine
III  2-methoxy-4-ethylamino-6-isopropylamino-1,3,5-triazine
IV  2-azido-4-sec.butylamino-6-methylmercapto-1,3,5-triazine
V  2-chloro-4-ethylamino-6-tert.butylamino-1,3,5-triazine, each at a rate of 0.25, 0.5, 0.75 and 1.0 kg/ha of active ingredient, and I + II, I + III, I + IV and I + V each at rates of 0.25 + 0.75, 0.75 + 0.25 and 0.5 + 0.5 kg/ha of active ingredient.

EXAMPLE 4

In a greenhouse experimental pots were filled with loamy sandy soil and sown with various seeds. The soil prepared in this way was then treated with the following individual active ingredients and mixtures thereof as an emulsion-dispersion:

I  N-n-propyl-N-β-chloroethyl-2,6-dinitro-4-trifluoromethylaniline
II  2-chloro-4-ethylamino-6-isopropylamino-1,3,5-triazine
III  2-chloro-4,6-diethylamino-1,3,5-triazine
IV  2-(2-chloro-4-ethylamino-1,3,5-triazine-6-ylamino)-2-methylpropionitrile, each at a rate of 0.25, 0.5, 0.75 and 1.0 kg/ha of active ingredient, and I + II, I + III and I + IV each at rates of 0.75+ 0.25, 0.25 + 0.75 and 0.5 + 0.5 kg/ha of active ingredient. After 3 to 5 weeks it was observed that the mixtures had a better herbicidal action that the individual active ingredients and the same compatibility with the crop plants. The results of the experiment may be seen from the following Table.

Table

| Active ingredient | I | | | | II | | | | III | | | | IV | | | |
|---|---|---|---|---|---|---|---|---|---|---|---|---|---|---|---|---|
| kg/ha | 0.25 | 0.5 | 0.75 | 1.0 | 0.25 | 0.5 | 0.75 | 1.0 | 0.25 | 0.5 | 0.75 | 1.0 | 0.25 | 0.5 | 0.75 | 1.0 |
| Crop plants | | | | | | | | | | | | | | | | |
| Zea mays | 0 | 0 | 0 | 0 | 0 | 0 | 0 | 0 | 0 | 0 | 0 | 0 | 0 | 0 | 0 | 0 |
| Triticum aestivum | 0 | 0 | 0 | 0 | 0 | 0 | 0 | 5 | 0 | 0 | 0 | 0 | 0 | 0 | 0 | 0 |
| Unwanted plants | | | | | | | | | | | | | | | | |
| Alopecurus myosuroides | 23 | 41 | 50 | 63 | 25 | 40 | 56 | 80 | 15 | 25 | 50 | 60 | 25 | 45 | 70 | 80 |
| Echinochloa crus galli | 32 | 50 | 58 | 70 | 10 | 28 | 40 | 50 | 3 | 5 | 6 | 20 | 10 | 15 | 18 | 20 |
| Lamium amplexicaule | 0 | 0 | 0 | 5 | 18 | 27 | 35 | 40 | 17 | 24 | 35 | 46 | 15 | 30 | 35 | 40 |

0 = no damage
100 = complete destruction

Table

| Active ingredient kg/ha | I+II | | | | I+III | | | | I+IV | |
|---|---|---|---|---|---|---|---|---|---|---|
| | 0.75+0.25 | 0.25+0.75 | 0.5+0.5 | 0.75+0.25 | 0.25+0.75 | 0.5+0.5 | 0.75+0.25 | 0.25+0.75 | 0.5+0.5 | |
| Crop plants | | | | | | | | | | |
| Zea mays | 0 | 0 | 0 | 0 | 0 | 0 | 0 | 0 | 0 | |
| Triticum aestivum | 0 | 0 | 0 | 0 | 0 | 0 | 0 | 0 | 0 | |
| Unwanted plants | | | | | | | | | | |
| Alopecurus myosuroides | 100 | 100 | 100 | 100 | 100 | 100 | 100 | 100 | 100 | |
| Echinochloa crus galli | 100 | 100 | 100 | 98 | 76 | 91 | 100 | 88 | 100 | |
| Lamium amplexicaule | 57 | 72 | 66 | 57 | 74 | 62 | 56 | 72 | 65 | |

0 = no damage
100 = complete destruction

I claim:

1. A herbicide composition containing a herbicidally effective amount of a mixture consisting essentially of
   a. N-n-propyl-N-β-chloroethyl-2,6-dinitro-4-trifluoromethylaniline and
   b. 2-methylmercapto-4,6-diisopropylamino-1,3,5-triazine; 2-methoxy-4-ethylamino-6-isopropylamino-1,3,5-triazine; 2-azido-4-sec.-butylamino-6-methylmercapto-1,3,5-triazine; 2-chloro-4-ethylamino-6-tert-butylamino-1,3,5-triazine; 2-chloro-4-ethylamino-6-isopropylamino-1,3,5-triazine; 2-chloro-4,6-diethyl-amino-1,3,5-triazine; or 2-(2-chloro-4-ethylamino-1,3,5-triazine-6-yl-amino)-2-methylpropionitrile in a weight ratio of compound a to compound b in the range of 3:1 to 1:3.

2. A process for controlling the growth of unwanted plants which comprises treating the soil in which the growth of unwanted plants is to be prevented with a herbicidally effective amount of a mixture of
   a. N-n-propyl-N-β-chloroethyl-2,6-dinitro-4-trifluoromethylaniline and
   b. 2-methylmercapto-4,6-diisopropylamino-1,3,5-triazine; 2-methoxy-4-ethylamino-6-isopropylamino-1,3,5-triazine; 2-azido-4-sec.-butylamino-6-methylmercapto-1,3,5-triazine; 2-chloro-4-ethylamino-6-tert-butylamino-1,3,5-triazine; 2-chloro-4-ethylamino-6-isopropylamino-1,3,5-triazine; 2-chloro-4,6-diethyl-amino-1,3,5-triazine, or 2-(2-chloro-4-ethylamino-1,3,5-triazine-6-yl-amino)-2-methylpropionitrile in a weight ratio of compound a to compound b in the range of 3:1 to 1:3.

* * * * *